(12) United States Patent
Münnig et al.

(10) Patent No.: US 6,953,869 B2
(45) Date of Patent: *Oct. 11, 2005

(54) PROCESS FOR WORKING UP SECONDARY COMPONENTS IN THE PREPARATION OF DINITROTOLUENE

(75) Inventors: Jürgen Münnig, Kaarst (DE); Dietmar Wastian, Dormagen (DE); Wolfgang Lorenz, Dormagen (DE); Berthold Keggenhoff, Krefeld (DE)

(73) Assignee: Bayer MaterialScience AG, Leverkusen (DE)

(*) Notice: Subject to any disclaimer, the term of this patent is extended or adjusted under 35 U.S.C. 154(b) by 0 days.

This patent is subject to a terminal disclaimer.

(21) Appl. No.: 10/878,079

(22) Filed: Jun. 28, 2004

(65) Prior Publication Data

US 2004/0267062 A1 Dec. 30, 2004

(30) Foreign Application Priority Data

Jun. 30, 2003 (DE) .......................................... 103 29 303

(51) Int. Cl.$^7$ ............................................ C07C 205/00
(52) U.S. Cl. ....................... 568/934; 568/927; 568/939; 568/940
(58) Field of Search ................................. 568/934, 927, 568/939, 940

(56) References Cited

U.S. PATENT DOCUMENTS

| 4,230,567 | A | 10/1980 | Larbig | 210/600 |
|---|---|---|---|---|
| 4,597,875 | A | 7/1986 | Carr et al. | 210/710 |
| 5,232,605 | A | 8/1993 | Baur et al. | 210/761 |
| 5,756,867 | A | 5/1998 | Hermann et al. | 568/934 |
| 5,762,802 | A | 6/1998 | Carr et al. | 210/626 |
| 6,506,948 | B1 | 1/2003 | Sawicki | 568/934 |
| 6,528,690 | B2 | 3/2003 | Klingler et al. | 568/934 |

FOREIGN PATENT DOCUMENTS

| DE | 101 43 800 C1 | 8/2002 |
|---|---|---|
| EP | 1 132 347 | 9/2001 |

*Primary Examiner*—J. Parsa
(74) *Attorney, Agent, or Firm*—Joseph C. Gil; N. Denise Brown

(57) ABSTRACT

The present invention relates to a process for working up organic secondary components which are formed in the one-stage or two-stage nitration of toluene to dinitrotoluene. These organic secondary components are present in the acidic and alkaline waste water from the dinitrotoluene washing step and in the aqueous distillate from the sulfuric acid concentration step, together with small amounts of mononitrotoluene and dinitrotoluene. This process comprises a) combining the acidic and alkaline waste waters from the washing step and the aqueous distillate from the sulfuric acid concentration step such that the resulting mixture has a pH below 5, b) separating the aqueous and organic phases which form by phase separation, and c) recycling the organic phase from step b) into the nitration process.

7 Claims, No Drawings

PROCESS FOR WORKING UP SECONDARY COMPONENTS IN THE PREPARATION OF DINITROTOLUENE

BACKGROUND OF THE INVENTION

The present invention relates to a process for working up or removing the organic secondary components obtained in the preparation of dinitrotoluene (DNT) by the nitration of toluene. These secondary components are separated with the process water from the crude DNT. It is necessary to treat these organic materials in order to be able to send the process waste water for a biological work-up.

In the conventional processes for the preparation of dinitrotoluene (DNT) from toluene and a mixture of sulfuric and nitric acids (nitrating acid), the acidic reaction water is distilled off in the sulfuric acid concentration step, and alkaline and acidic wash water from the purification of the DNT, are obtained as waste waters. In addition to mononitrotoluene and dinitrotoluene, this process waste water contains nitration by-products such as mononitrocresols, dinitrocresols and trinitrocresols (hereafter referred to globally as nitrocresols), picric acid and nitrobenzoic acids. These substances have to be removed from the waste water because aromatic nitro compounds do not easily degrade in biological waste water treatment plants and have properties toxic to bacteria.

The current state of the art for the treatment of organic secondary components in the nitration of aromatic compounds is as follows:

U.S. Pat. No. 6,506,948 describes the work-up of wash water from the purification of DNT prepared from toluene and nitrating acid. The DNT is recovered from acidic and alkaline wash water, with the organic secondary components remaining in the alkaline aqueous phase. A work-up of these secondary components is not, however, described in U.S. Pat. No. 6,506,948. Rather, there is merely a general reference to a possible chemical pretreatment (oxidation) or physical pretreatment (adsorption) prior to discharge into a biological waste water treatment plant.

The treatment of nitrocresols, which are separated from the product stream in the alkaline DNT washing step, can be effected by oxidative degradation with nitric acid at elevated temperatures according to EP A1 0 962 446. As described therein, however, this requires its own additional process stage. Temperatures of up to 180° C. are necessary for this process stage. In addition, an aftertreatment by adsorption on activated charcoal or a corresponding work-up in a biological waste water treatment plant is still required.

For the degradation of nitro compounds in the alkaline wash water from the work-up of nitrobenzene, U.S. Pat. No. 5,232,605 describes treating this waste water with nitric acid at temperatures of up to 290° C. and at pressures of up to 130 bar. After this separate additional process step, the waste water can be sent to a biological waste water treatment plant.

In the context of the preparation of nitrobenzene, U.S. Pat. No. 4,230,567 also describes the degradation of nitrophenols in an additional process step at elevated pressure and temperature. After alkaline washing of the nitrobenzene, the wash water is exposed to temperatures of 150° C. to 500° C. at pressures of 50 to 350 bar under an inert gas atmosphere.

After alkaline washing of the DNT, the process of U.S. Pat. No. 4,597,875 requires acidic precipitation of the nitrocresol components from the wash water and their mechanical settling. Then, the nitrocresol compounds are burnt in a suitable combustion process. Here again, however, an additional process step is required for working up the nitrocresol components.

The object of the present invention is to provide a simple and economic process for the separation and treatment of unwanted secondary components of the nitration. Surprisingly, this is achieved by means of steps that are simple in terms of process technology, particularly when compared with existing processes, and without additional process steps and feed materials that are foreign to the nitration process.

SUMMARY OF THE INVENTION

The present invention relates to a process for working up or removing organic secondary components which are formed during the nitration of toluene to dinitrotoluene. The nitration of toluene to dinitrotoluene may be a one-stage or a two-stage process. These organic secondary components are present in the acidic and alkaline waste water from the dinitrotoluene washing step, and in the aqueous distillate from the sulfuric acid concentration step, together with small amounts of mononitrotoluene and dinitrotoluene. The process comprises:

a) combining (1) the acidic and alkaline waste waters from the washing step, and (2) the aqueous distillate from the sulfuric acid concentration step such that the resultant mixture has a pH below 5 (measured at 70° C.), b) separating the resultant aqueous and organic phases by phase separation, and c) recycling the organic phase from step b) into the nitration process.

In the conventional process for the nitration of aromatic hydrocarbons, the hydrocarbon is reacted with a mixture of sulfuric acid and nitric acid (nitrating acid). In the case of the nitration of toluene to dinitrotoluene, a two-stage nitration is one of the general current processes along with the one-stage nitration process as described in, for example, U.S. Pat. No. 6,528,690, believed to correspond to EP A 2-908 442, the disclosure of which is herein incorporated by reference. In the two-stage process, toluene is first converted to mononitrotoluene (MNT) with nitric acid and sulfuric acid (monostage). After separation of the resulting reaction mixture into MNT and an acidic phase, which can be carried out in static settlers or dynamic settlers, the MNT is reacted with nitric acid and sulfuric acid to give dinitrotoluene (DNT) (distage). The sulfuric acid phase from the mono-stage is concentrated. The sulphuric acid feed for the di-stage is concentrated acid. The reaction mixture of the di-stage is separated into an organic phase, i.e. the crude DNT, and an acidic phase, it being possible for the acidic phase to be used as sulfuric acid feed for the mono-stage or concentrated. This reaction mixture of the di-stage can likewise be separated in static or dynamic settlers.

All processes for the preparation of DNT by the nitration of toluene with nitrating acid produce two material streams which have to be sent for a further work-up. These streams are the crude DNT and the sulfuric acid diluted by the reaction water and by the water present in the nitric acid which was used.

The crude DNT generally consists substantially of the desired reaction product with up to 1.5 wt. % of sulfuric acid, 0.5 wt. % to 1.2 wt. % of excess nitric acid and up to approx. 1 wt. % of secondary components of the nitration. These secondary components are substantially nitrocresols, picric acid and nitrobenzoic acids. In the conventional process, acids and secondary components are removed from the crude DNT in two to four washing stages with water. The wash water introduced in this process may contain a base in at least one washing stage. Conventionally, the base is sodium hydroxide or sodium carbonate in concentrations of from 2 to 10 wt. %. Whereas the neutral aqueous washing step extensively removes sulfuric acid and nitric acid from the nitration product, the alkaline washing step also transfers salt-forming organic components such as, for example nitrocresols, picric acid and nitrobenzoic acids, to the aqueous phase.

Other than the one-stage alkaline washing step and the last aqueous washing step, fresh water or wash water from a subsequent stage, introduced in countercurrent, can be used as wash water. However, the wash water may also be fresh water, demineralized water, or any other water of suitable quality from a process subsequent to the nitration process described above.

The amounts of wash water used for the washing steps preferably range from 15 to 90 parts by weight, and more preferably from 50 to 65 parts by weight of wash water, per 100 parts by weight of DNT.

Depending on the quantity of wash water used and the source of the wash water feed, the neutral aqueous washing step produces an acidic process waste water having preferred acid contents of from 1.0 to 3.0 wt. % of nitric acid and from 2.0 to 6.0 wt. % of sulfuric acid, and a DNT content of several thousand ppm. The concentration of organic nitration by-products (i.e. organic secondary components) in the process waste water is generally between 300 and 900 ppm.

The waste water stream of the alkaline washing step generally contains from 3.0 to 7.0 wt. % of organic nitration by-products, which consist substantially of nitrocresols, picric acid and nitrobenzoic acids, in the form of their water-soluble salts. This waste water stream can further contain several thousand ppm of DNT, together with from 2.0 to 4.0 wt. % of nitric acid and from approx. 0.6 to 1.2 wt. % of sulfuric acid in the form of their water-soluble salts. The waste water stream of the alkaline washing step has a pH >7.0, and preferably >7.5, as measured at 80° C.

The washing stages are carried out in suitable apparatuses and preferably in scrubber or extraction columns or in mixer-settlers.

The dilute sulfuric acid from the nitration can comprise from 70 to 90 wt. %, preferably from 70 to 80 wt. % and most preferably from 75 to 79 wt. % of sulfuric acid. It can also contain from 0.005 to 0.5 wt. %, and preferably from 0.005 to 0.05 wt. % of nitric acid, up to 3.0 wt. % of MNT, and from 0.2 to 2.0 wt. % of DNT. The acid to be worked up also contains up to 0.2 wt. % of organic secondary components consisting substantially of nitrocresols, picric acid and nitrobenzoic acids. Examples of possible processes for concentration of the dilute sulfuric acid are, inter alia, the Pauling process at normal pressure [as described by, for example, Bodenbrenner, von Plessen, Vollmüller, Dechema-Monogr. 86 (1980), 197], which produces approx. 97% sulfuric acid, and vacuum evaporation as described in U.S. Pat. No. 6,332,949, believed to correspond to DE-A1-196 42 328, the disclosure of which is herein incorporated by reference, which can also yield up to 97% sulfuric acid. As well as the desired sulfuric acid, one or more aqueous phases with a sulfuric acid content of from 0.2 to 1.0 wt. % and preferably from 0.2 to 0.6 wt. %, an MNT content of 0.7 to 7.0 wt. % and a DNT content of 2.0 to 6.0 wt. % are generally obtained after condensation of the vapors. Other organic compounds are conventionally present in concentrations of up to 0.4 wt. %. The organic components in the distillate are dissolved or dispersed.

In accordance with the process of the present invention, the waste water streams of the neutral and alkaline DNT washing steps and the sulfuric acid concentration step are combined. The aqueous phases from the nitration are made up of several individual streams, preferably two to four, with at least one of the individual streams originating from the neutral aqueous washing step (acidic wash water) and at least one individual stream originating from the alkaline washing step (alkaline wash water). The aqueous phases from the sulfuric acid concentration step are made up of one or more individual streams with contents of acids and organic components.

The process waste water streams can be combined in an appropriate tank with a dynamic mixing element, or, for example, by means of a static mixing unit. After the streams have been combined, the pH of the resulting mixture is below 5 as measured at 70° C., and preferably below 2. From this mixture, an organic phase settles out. If the alkaline washing step is carried out with very large amounts of base, it is theoretically possible to obtain a pH of $\geq 5$ when the waste waters from the DNT washing step and the distillate from the sulfuric acid concentration step are combined. The amount of alkaline waste water used, for example, would then have to be reduced accordingly in order to bring the pH below 5. This organic phase consists of MNT and DNT together with nitration by-products. These nitration by-products are predominantly nitrocresols, picric acid and nitrobenzoic acids. If carbonate is used in the alkaline washing step, there must be an appropriate venting facility at, or close to, the point where the streams are combined. To separate off the organic phase which is formed, the combined waste water streams are then sent to a suitable settling vessel, and allowed to separate by phase separation. After this settling step, the aqueous phase is sent separately for a further waste water work-up.

MNT can additionally be fed in when the process waste water streams are combined. The addition of MNT can assist the phase separation, and by lowering the solidification point of the organic phase, can facilitate the transportation of this mixture of materials in the process. The amounts of MNT added are preferably from 0.2 to 9 parts by weight, and more preferably from 0.5 to 4.0 parts by weight of MNT, per 100 parts by weight of process waste water.

Because of the density difference, the organic phase, which consists predominantly of MNT, DNT, nitrocresols, picric acid and nitrobenzoic acids, generally forms the heavier phase. In the process according to the present invention, this organic phase is recycled from the settling vessel back into the nitration process. Here, the organic phase can be recycled directly into the nitration reactor in the case of the one-stage nitration process (e.g. adiabatic dinitration), or into the nitration reaction for MNT preparation (mono-stage) or into the nitration reaction for DNT preparation (di-stage) in the case of the two-stage process. The MNT and DNT entrained with the waste waters is recovered by recycling into the nitration process and, surprisingly, the organic secondary components, such as nitrocresols, picric acid and nitrobenzoic acids, are oxidatively degraded under the oxidative conditions by the nitric acid present in the nitration process. This is shown, for example, by the formation of oxalic acid as a degradation product.

Thus, the advantage of the present process is that the unwanted organic secondary components which are formed in the nitration process, then separated off by the DNT washing step, and subsequently combining of the waste waters with settling-out of the organic materials, can easily be degraded without an additional process step and without the introduction of additional substances foreign to the process. Also, MNT and DNT entrained with the process waste waters are recovered by this process.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

10 g of an organic phase mixture, obtained by combining the process waste waters from the DNT washing step and the sulfuric acid concentration step, with subsequent phase separation, were added at 70° C. to 500 g of a nitrating acid mixture consisting of 79 wt. % of sulfuric acid, 10 wt. % of nitric acid and 11 wt. % of water.

The organic phase mixture had the following composition:

| | |
|---|---|
| 13.2% | MNT |
| 69.0% | DNT |
| 17.0% | Nitrocresols |
| 0.8% | Picric acid |

The following concentration profile was determined in the reaction mixture over the observation period:

| Reaction time [min] | Σ Nitrocresols [ppm] | Picric acid [ppm] |
|---|---|---|
| 0 | 3342 | 149 |
| 1 | 1764 | 144 |
| 5 | 895 | 143 |
| 15 | 672 | 141 |
| 30 | 537 | 134 |
| 60 | 398 | 132 |
| 120 | 255 | 127 |
| 360 | 115 | 115 |

The nitrocresol concentration was reduced by 96.6 wt. % over the reaction time.

The picric acid concentration decreased by 22.8 wt. %.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for removing organic secondary components which are formed during the nitration of toluene to dinitrotoluene, and which are present in the acidic and alkaline waste water from the dinitrotoluene washing step and in the aqueous distillate from the sulfuric acid concentration step, together with small amounts of mononitrotoluene and dinitrotoluene, comprising:

a) combining (1) the acidic and alkaline waste waters resulting from the washing step of the nitration process, and (2) the aqueous distillate from the sulfuric acid concentration step such that the resultant mixture has pH below 5, b) separating the resultant aqueous and organic phases by phase separation, and c) recycling the organic phase from step b) into the nitration process.

2. The process of claim 1, wherein a) combining of the aqueous waste waters is in a static mixer with a downstream venting facility.

3. The process of claim 1, additionally comprising mixing the combined aqueous phases with mononitrotoluene.

4. The process of claim 1, wherein the organic secondary components additionally comprise nitrocresols.

5. The process of claim 1, wherein the organic secondary components additionally comprise picric acid.

6. The process of claim 1, wherein the organic secondary components additionally comprise nitrobenzoic acids.

7. The process of claim 1, wherein the nitration of toluene to dinitrotoluene is selected from the group consisting of a one-stage nitration process and a two-stage nitration process.

* * * * *